US006464979B1

(12) United States Patent
Murdin et al.

(10) Patent No.: US 6,464,979 B1
(45) Date of Patent: *Oct. 15, 2002

(54) CHLAMYDIAL VACCINES AND METHODS OF PREPARATION THEREOF

(75) Inventors: Andrew D. Murdin, Newmarket; Brian J. Underdown, Hamilton, both of (CA)

(73) Assignee: Aventis Pasteur Limited, Toronto (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/713,236

(22) Filed: Sep. 12, 1996

(51) Int. Cl.[7] .................. A61K 39/00; A61K 39/38; A61K 39/02; A61K 39/118

(52) U.S. Cl. ................. 424/184.1; 424/234.1; 424/263.1

(58) Field of Search ............ 424/184.1, 234.1, 424/263.1

(56) References Cited

FOREIGN PATENT DOCUMENTS

EP 415794 * 3/1991

OTHER PUBLICATIONS

Batteiger et al. Journal of General Microbiology 139:2965–2972, 1993.*
Brooks et al. Medical Microbiology 20th ed. Appleton & Lang, Connecticut, 1995 pp. 294–302.*
Rossini et al. Journal of Immunological Research 4(4):189–196, 1992.*
Jones, G. E. et al: "Efficacy trials with tissue–culture grown, inactivated vaccines against chlamydial abortion in sheep", Vaccine, vol. 13, No. 8. 1995, pp. 715–723, XP004057519.
Sandbulte J. et al: "Evaluation of Chlamydia psittaci subfraction of subunit preparations for their protective capacities." Veterinary Microbiology, vol. 48, No. 3–4, Feb. 1996, pp. 269–282, XP002050284.
Campos M. et al: "A Chlamydial Major Outer Membrane Protein Extract as a Trachoma Vaccine Candidate." Investigative Ophthalmology & Visual Science 36 (8). 1995. 1477–1491. ISSN: 0146–0404, XP002050285.
Pal S. et al: "Immunization with an acellular vaccine consisting of the outer membrane complex of Chlamydia trachomatis induces protection against a genital challenge." Infection and Immunity, vol. 65, No. 8, Aug. 1997, pp. 3361–3369, XP002050286.
EP 0 059 624A (Univ. California) Sep. 8, 1982.
Grayston, J.T. and S.–P. Wang. 1975. New Knowledge of Chlamydiae and the Diseases They Cause. J. Infect. Dis., 132: 87–104.

Grayston, J.T., S.–P. Wang, L.–J. Yeh, and C.–C. Kuo. 1985. Importance of Reinfection in the Pathogenesis of Trachoma. Rev. Infect. Dis. 7:717–725.
Taylor, H.R., S.L. Johnson, R.A. Prendergast, J. Schachter, C.R. Dawson and A.M. Silverstein, 1982. An Animal Model of Trachema. II. The Importance of Repeated Infection. Invest. Opthalmol. Visual. Sci. 23 507–515.
Taylor, H.R., R.A. Prendergast, C.R. Dawson, J. Schachter and A.M. Silverstein, 1981. An Animal Model for Cicatrizing Trachoma. Invest. Opthalmol. Sci. 21 422–433.
Caldwell, H.D., S. Stewart, S. Johnson and H. Taylor. 1987. Tear and Serum Antibody Response to Chlamydia trachomatis Antigens During Acute Chlamydial Conjunctivitis in Monkeys as Determined by Immunoblotting. Infect. Immun. 55: 93–98.
Wang, S.–P., C.–C. Kuo, R.C. Barnes, R.S. Stephens and J.T. Grayston. 1985. Immunotyping of Chlamydia trachomatis with Monoclonal Antibodies. J. Infect. Dis 152:791–800.
Nichols, R.L., R.E. Oertley, C.E,O. Fraser, A.B. MacDonald, and D.E. McComb. 1973. Immunity to Chlamydial Infections of the Eye. VI. Homologous Neutralization of Trachoma Infectivity for the Owl Monkey Conjuctivae by the Eye Secretions From Humans With Trachoma. J. Infect. Dis. 127: 429–432.
Orenstein, N.S., J.D. Mull and S.E. Thompson III. 1973. Immunity to Chlamydial Infections of the Eye. V. Passive Transfer of Antitrachoma Antibodies to Owl Monkeys. Infect. Immun. 7:600–603.
Ramsey, KH, Rank, R.G., (Mar. 1991). Resolution of Chlamydia Genital Infection with Antigen–Specific T–Lymphocyte Lines. Infect. and Immun. 59:925–931.
Magee, DM, William, DM, Smith, JG, Bleicker, CA, Grubbs, BG, Schachter, J. and Rank, RG., (1995). Role of CD8 T Cells in Primary Chlamydia Infection. Infect. Immun. Feb. 1995. 63: 516–521.
Su, H. and Caldwell, HD., (1995) CD4+ T Cells Play a Significant Role in Adoptive Immunity to Chlamydia trachomatis Infection of the Mouse Genital Tract. Infect. Immun. Sep. 1995, 63: 3302–3308.

(List continued on next page.)

Primary Examiner—Mark Navarro
(74) Attorney, Agent, or Firm—Sim & McBurney (57) ABSTRACT

Immunogenic compositions including vaccines are described that comprise an outer membrane antigen extract of a strain of Chlamydia and are effective in protection against disease caused by Chlamydia infection. The immunogenic compositions may comprise the major outer membrane protein (MOMP) of Chlamydia which may be in a homooligomeric form or complexed with at least one other antigen of Chlamydia. The immunogenic composition may include an immunostimulating complex (ISCOM) and the outer membrane antigen may be incorporated therein. The immunogenic compositions have utility as chlamydial vaccines and in diagnostic applications.

9 Claims, 7 Drawing Sheets

OTHER PUBLICATIONS

Magee, DM, Williams, DM., Smith, JG., Bleicker, CA., Grubbs, BG, Schachter, J. and Rank, RG., (1995) Role of CD8 T Cells in Primary Chlamydia Infection., Infect. Immun. Feb. 1995. 63: 516–521.

Beatty, PR., and Stephens RS., 1994, CD8+ T Lymphocyte–Mediated Lysis of Chlamydia–Infected L Cells Using an Endogenous Antigen Pathway., Journal of Immun. 1994, 153:4588.

Starnbach, MN. Bevan, MJ. and Lampe, MF. (1994), Protective Cytotoxic T. Lymphocytes are Induced During Murine Infection With *Chlamydia trachomatis*, Journal of Immun. 1994, 153:5183.

Starnbach, MN. Bevan, MJ. and Lampe, MF., (1995), Murine Cytotoxic T. Lymphocytes Induced Following *Chlamydia trachomatis* Intraperitonal or Genital Tract Infection Respond to Cells Infected With Multiple Serovars., Infect. & Immun. Sep. 1995, 63: 3527–3530.

Igietseme, JU, (1996), Molecular Mechanism of T–Cell Control of Chlamydia in Mice: Role of Nitric Oxide in vivo. Immunology 1996, 88:1–5.

Igietseme, JU, (1996), The Molecular Mechanism of T–Cell Control of Chlamydia in Mice: Role of Nitric Oxide. Immunology 1996, 87:1–8.

Ward, M.E. 1992. Chlamydial Vaccines—Future Trends. J. Infection 25, Supp. 1:11–26.

Caldwell, H.D., J. Kromhout and J. Schachter. 1981. Purification and Partial Characterization of the Major Outer Membrane Protein of *Chlamydia trachomatis*. Infect. Immun. 31:1161–1176.

Bavoil, P., Ohlin, A. and Schachter, J., 1984. Role of Disulfide Bonding in Outer Membrane Structure and Permeability in *Chlamydia trachomatis*. Infect. Immun., 44: 479–485.

Campos, M., Pal, Sukumar, O'Brian, T.P., Taylor, H.R., Prendergast, R.A., and Whittum–Hudson, J.A., 1995., A Chlamydia Major Outer Membrane Protein Extract as a Trachoma Vaccine Candidate., Invest. Opthalmol. Vis. Sci. 36: 1477–1491.

Zhang Y.–X., S.J. Stewart, and H.D. Caldwell. 1989. Protective Monoclonal Antibodies to *Chlamydia trachomatis* Serovar– and Serogroup–Specific Major Outer Membrane Protein Determinants. Infect. Immun. 57:636–638.

Zhang, Y.–X., S. Stewart, T. Joseph, H.R. Taylor and H.D. Caldwell. 1987. Protective Monoclonal Antibodies Recognise Epitopes Located on the Major Outer Membrane Protein of *Chlamydia trachomatis*. J.Immunol. 138:575–581.

Yuan, Y., Y.–X. Zhang, N.G. Watkins, and H..D. Caldwell. 1989. Nucleotide and Deduced Amino Acid Sequences for the Four Variable Domains of the Major Outer Membrane Proteins of the 15 *Chlamydia trachomatis* Serovars. Infect. Immun. 57:104–1049.

Su, H. and H.D. Caldwell, H.D. 1992. Immunogenicity of a Chimeric Peptide Corresponding to T–Helper and B–Cell Epitopes of the *Chlamydia trachomatis* Major Outer Membrane Protein. J. Exp. Med. 175:227–235.

Su, H., N.G. Watkins, Y.–X. Zhang and H.D. Caldwell. 1990. *Chlamydia trachomatis*–Host Cell Interactions: Role of the Chlamydial Major Outer Membrane Protein as an Adhesin. Infect.Immun. 58:1017–1025.

Peeling, R., I.W. McClean and R.C. Brunham. 1984. In vitro Neutralization of *Chlamydia trachomatis* with Monoclonal Antibody to an Epitope on the Major Outer Membrane Protein. Infect.Immun. 46:484–488.

Lucero, M.E. and C.–C. Kuo. 1985. Neutralization of *Chlamydia trachomatis* Cell Culture Infection by Serovar Specific Monoclonal Antibodies. Infect. Immun. 50: 595–597.

Baehr, W., Y.–X. Zhang, T. Joseph, H. Su, F.E. Nano, K.D.E. Everett and H.D. Caldwell. 1988. Mapping Antigenic Domains Expressed by *Chlamydia trachomatis* Major Outer Membrane Protein Genes. Proc. Natl. Acad. Sci. USA, 85:4000–4004.

Stephens, R.S., E.A. Wagar and G.K. Schoolnik. 1988. High–Resolution Mapping of Serovar–Specific and Common Antigenic Determinants of the Major Outer Membrane Protein of *Chlamydia trachomatis*. J. Exp. Med. 167:817–831.

Conlan, J.W., I.N. Clarke and M.E. Ward. 1988. Epitope Mapping With Solid–Phase Peptides: Identification of Type–, Subspecies–, Species–, and Genus–Reactive Antibody Binding Domains on the Major Outer Membrane Protein of *Chlamydia trachomatis*. Mol. Microbiol. 2: 673–679.

Conlan, J.W., S. Ferris, I.N. Clarke, and M.E. Ward. 1990. Isolation of Recombinant Fragments of the Major Outer Membrane Protein of *Chlamydia trachomatis*: Their Potential as Subunit Vaccines. J. Gen. Microbial. 136: 2013–2020.

Morrison, R.P., D.S. Manning, and H. D. Caldwell. 1992. Immunology of *Chlamydia trachomatis* Infections. P. 57–84 in T.C. Quinn (ed) Sexually Transmitted Diseases. Raven Press Ltd., NY.

Kersten, G.F.A. and Crommelin, D.J.A. 1995. Liposomes and ISCOMs as Vaccine Formulations. Biochimica et Biophysica Acta 1241 (1995) 117–138.

Morein, B., Fossum, C., Lovgren, K. and Hoglund, S., 1990. The ISCOM—A Modern Approach to Vaccines. Seminars in Virology, vol. 1, 1990: pp 49–55.

Mowat & Reid, 1992. Preparation of Immune Stimulating Complexes (ISCOMs) as Adjuvants. Current Protocols in Immunology 1992, Supplement 4: 2.11.1 to 2.11.12.

* cited by examiner

Extraction using
1% Octyl glucoside

FIG. 2B.

Extraction using
1% Mega 10

FIG. 2C.

Extraction using
0.75% Octyl glucoside
+ 0.25% Mega 10

Figure 3.

1. Sarkosyl-soluble fraction probed with anti-HSP60
2. MAE probed with convalescent mouse serum
3. MAE probed with anti-HSP60
4. MAE probed with anti-serovar L2
5. MAE probed with mAb anti-MOMP

Figure 4.

R = MAE analysed by reducing SDS-PAGE
NR = MAE analysed by non-reducing SDS-PAGE
MW = Approximate molecular weight of MOMP and oligomers

CHLAMYDIAL VACCINES AND METHODS OF PREPARATION THEREOF

FIELD OF INVENTION

The invention relates to the field of immunology and, in particular, relates to vaccines against Chlamydia.

BACKGROUND TO THE INVENTION

*Chlamydia trachomatis* is a species of the genus Chlamydiaceae, order Chlamydiales. *C. trachomatis* infects the epithelia of the conjunctivae and the genital tract, causing trachoma and a variety of sexually transmitted diseases (STDs) which can lead to, respectively, blindness or infertility. There are at least 15 serovars of *C. trachomatis*, of which A, B, and C are causative agents of trachoma, while serovars D, E, F, G, H, I, J, and K are the most common causative agents of chlamydial STDs. *C. trachomatis* infections are endemic throughout the world. Trachoma is the leading cause of preventable blindness in developing nations, and it is estimated that 600 million people suffer from trachoma worldwide, with as many as 10 million of them being blinded by the disease. In the United States there are an estimated 3 million cases per year of STDs caused by *C. trachomatis*.

The pathogenesis of trachoma involves repeated ocular infections and the generation of a deleterious hypersensitivity response to chlamydial antigen(s) (refs 1 to 4 —Throughout this specification, various references are referred to in parenthesis to more fully describe the state of the art to which this invention pertains. Full bibliographic information for each citation is found at the end of the specification, immediately following the claims. The disclosures of these references are hereby incorporated by reference into the present disclosure). The available evidence supports the hypothesis that both secretory IgA and cell-mediated immune responses are important components of protection. Ocular infection in a primate model induces rapid and persistent production of IgA in tears, whereas the presence of IgG in tears is transient, corresponding to the period of peak conjunctival inflammation (ref. 5). protective immunity following experimental ocular infection in a sub-human primate model is homotypic and resistance to ocular challenge correlates with the presence of serovar-specific antibodies in tears (refs. 1, 2, 6). Tears from infected humans neutralised the infectivity of homologous but not heterologous trachoma serovars for owl monkey eyes (ref. 7) whereas passive humoral immunization with antitrachoma antibodies was not protective (ref. 8). Several lines of evidence indicate the importance of cell-mediated responses in protection from or clearance of chlamydial infection. B-cell deficient mice can resolve infection, whereas nude mice become persistently infected. Adoptive transfer of at least some chlamydia-specific T-cell lines or clones can cure persistently infected nude mice, and this anti-chlamydial activity is probably a function of the ability of the T-cells to secrete interferony (refs. 9 to 17).

past attempts to develop whole-cell vaccines against trachoma have actually potentiated disease by sensitizing vaccinees (refs. 1, 2). Sensitization has been determined to be elicited by a 57 kD stress response protein (SRP) (HSP60) present in all serovars of *C. trachomatis*. Repeated exposure to the 57 kD SRP can result in a delayed hypersensitivity reaction, causing the chronic inflammation commonly associated with chlamydial infections. Thus, an immunogenic preparation capable of inducing a strong and enduring mucosal neutralising antibody response and a strong cellular immune response without sensitizing the vaccinee would be useful (ref. 18).

A most promising candidate antigen for the development of a vaccine is the chlamydial major outer membrane protein (MOMP) (refs. 19 to 21). Other surface proteins and the surface lipopolysaccharide are also immunogenic, but the antibodies they induce have not been found to be protective (ref. 22, 23). The MOMP, which is the predominant surface protein, is an integral membrane protein with a mass of about 40 kDa which, with the exception of four variable domains (VDs) designated I, II, III, and IV, is highly conserved amongst serovars. The sequences of all four VDs have been determined for fifteen serovars (ref. 24, 25). Antibodies capable of neutralising chlamydial infectivity recognize the MOMP (ref. 26, 27, 28, 29). Epitopes to which MOMP-specific neutralising monoclonal antibodies bind have been mapped for several serovars (refs. 22, 23, 30, 31, 32, 33, 34), and represent important targets for the development of synthetic or subunit vaccines. The binding sites are contiguous sequences of six to eight amino acids located within VDs I or II, and IV, depending on the serovar. Subunit immunogens (e.g. isolated MOMP or synthetic peptides) containing MOMP epitopes can induce antibodies capable of recognising intact chlamydiae (ref. 26). However, conventionally administered subunit immunogens are generally poor inducers of mucosal immunity. It would be useful to formulate chlamydial antigens in such a way as to enhance their immunogenicity and to elicit both humoral and cell-mediated immune responses.

Immune stimulating complexes (ISCOMs) are cage-like structures formed from a mixture of saponins (or saponin derivatives), cholesterol and unsaturated fatty acids. The components of ISCOMs are held together by hydrophobic interactions, and consequently proteins which are naturally hydrophobic (such as MOMP) or which have been treated to expose or add hydrophobic residues can be efficiently incorporated into the ISCOMs as they form (ref. 35, 36, 37).

*C. trachomatis* naturally infects the mucosal surfaces of the eye and genital tract, and secretory IgA cellular responses are probably important components of protection. Consequently, it would be useful for a chlamydial vaccine to induce a mucosal immune response including both cellular and antibody components.

*C. trachomatis* infection may lead to serious disease. It would be advantageous to provide outer membrane antigen extracts of Chlamydia, including the major outer membrane protein of Chlamydia, particularly in substantially the native conformation for antigens in immunogenic preparations including vaccines, and immunogens and the generation of diagnostic reagents.

SUMMARY OF THE INVENTION

The present invention provides a novel immunogenic form of chlamydial MOMP which is useful in providing protection against chlamydial diseases, as well as methods of preparing such materials.

In accordance with one aspect of the invention, there is provided an immunogenic composition, comprising an outer membrane antigen extract (MAE) of a strain of Chlamydia, which may be *Chlamydia trachomatis,* and an immunostimulating complex (ISCOM).

The MAE may comprise the major outer membrane protein (MOMP) of the strain of Chlamydia. The MOMP may be in an oligomeric form and/or may be complexed with at least one other antigen of the strain of Chlamydia.

Such oligomers and complexes may have a molecular weight of from about 45 to about 125 kDa. The procedure described herein for preparation of the MAE, specifically MOMP, produces material which is substantially free from the heat shock protein HSP60 of the strain of Chlamydia. The immunogenic composition provided herein may be in the form of the MEA incorporated into ISCOMs.

The immunogenic compositions provided herein may be employed, in accordance with another aspect of the invention, to protect a host against disease caused by a strain of Chlamydia by administering to the host an effective amount of the immunogenic composition. Such administration may be to a mucosal surface to produce a mucosal immune response. Alternatively, any other convenient means of administration may be employed to produce the desired immune response. The administration may be to the mucosal surface of the host by intranasal administration and may produce a genital tract immune response.

The present invention further includes a method of producing an outer membrane antigen extract of a strain of Chlamydia using a combination of two or more detergents including non-ionic detergents. Accordingly, in a further aspect of the invention, there is provided such a method which comprises:

detergent extracting elementary bodies (EBs) of the strain of Chlamydia in the presence of a reducing agent for disulphide bonds to solubilize cytoplasmic material away from outer membrane material;

separating the solubilized cytoplasmic material from the outer membrane materials, detergent extracting the outer membrane material using at least two non-ionic detergents in the presence of a reducing agent for disulphide bonds to solubilize outer membrane antigens; and separating the solubilized outer membrane antigens from residual unextracted membrane-associated material to provide the outer membrane antigen extract.

In one embodiment of this aspect of the invention, the at least two non-ionic detergents comprise a N-methyl glucamide non-ionic detergent which may be selected from heptanoyl-, octanoyl-, nonanoyl- and decanoyl-N-methyl glucamide, and a glucopyranoside non-ionic detergent, which may be selected from n-hexyl-β-D-, n-heptyl-β-D-, n-octyl-α-D-, n-octyl-β-D-, n-nonyl-β-D-, n-decyl-α-D- and n-decyl-β-D-glucopyranoside. Such glucopyranosides are sometimes termed glucosides. The two non-ionic detergents may be employed in a weight ratio from about 1:10 to about 10:1. The use of the two detergents enables a high degree of recovery of outer membrane antigen which remain soluble at a wide range of temperature of storage.

The procedure described herein for the preparation of the outer membrane extract produces a novel Chlamydial antigen preparation. Accordingly, in an additional aspect of the present invention, there is provided a purified outer membrane antigen extract of a strain of Chlamydia in the form of an aqueous solution of antigen in the presence of at least two non-ionic detergents and a reducing agent.

In such composition, the purified outer membrane antigen extract comprises the major outer membrane protein (MOMP) of the strain of Chlamydia, particularly substantially in its native conformation. The MOMP usually comprises homooligomers and heterooligomers thereof, which may have the molecular weights from about 45 to about 125 kDa.

The provision of such novel purified materials enables there to be provided, in accordance with an additional aspect of the invention, a vaccine composition effective for protection against disease caused by a strain of Chlamydia, including *Chlamydia trachomatis,* comprising purified and non-denatured major outer membrane protein (MOMP) of the strain of Chlamydia substantially in its native conformation.

Such MOMP may be in the form of unaggregated homooligomers and heterooligomers. The vaccine composition may be in the form of immunostimulatory complexes (ISCOMs) incorporating the MOMP. The vaccine composition may further comprise at least one other chlamydial or non-chlamydial antigen.

The present invention further extends, in a further aspect of the invention, to a method for producing a vaccine against disease caused by a strain of Chlamydia, including *Chlamydia trachomatis,* comprising:

administering the vaccine composition provided herein to a test host to determine an amount and a frequency of administration thereof to confer protection against disease caused by the strain of Chlamydia; and formulating the vaccine in a form suitable for administration to a treated host, which may be a human, in accordance with the determined amount and frequency of administration.

BRIEF DESCRIPTION OF THE DRAWINGS

The present invention will be further understood from the following description with reference to the accompanying drawings, in which:

FIG. 3 shows the results of an immunoblot demonstrating the presence of HSP60 in the Sarkosyl-soluble fraction (lane 1) but not in the MAE (lane 3). FIG. 3 also shows the presence in the MAE of MOMP (lanes 2 and 5) and several other antigens (lanes 2 and 4);

GENERAL DESCRIPTION OF INVENTION

The present invention provides novel techniques which can be employed for preparing outer membrane antigen extracts from Chlamydia, including purified major outer membrane protein from Chlamydia. Any Chlamydia strain, including *C. trachomatis,* may be conveniently used to provide the outer membrane antigen extracts as provided herein. Such strains are generally available from clinical sources and from bacterial culture collections.

Figure 1:
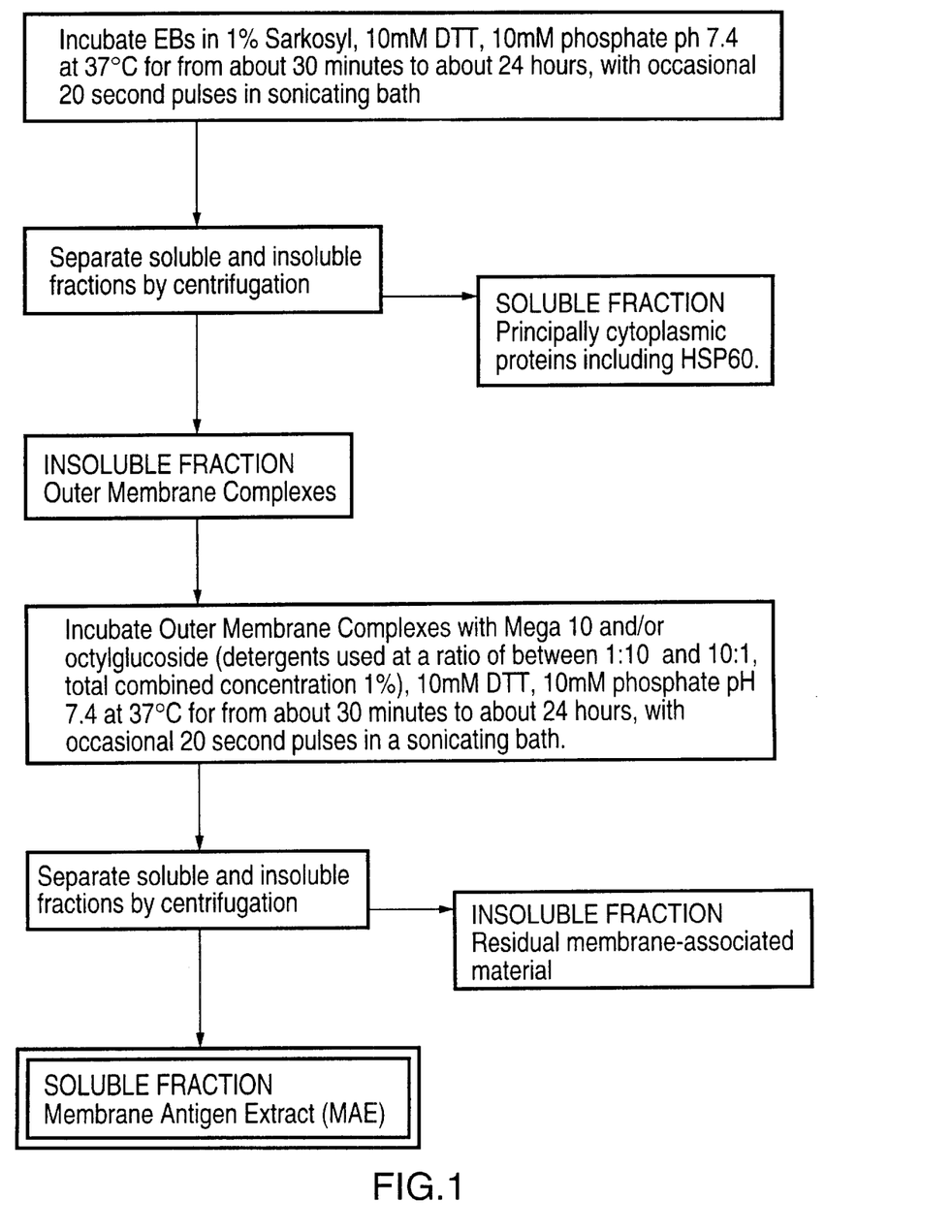
FIG. 1 shows the procedure for the purification of the chlamydial membrane antigen extract (MAE), in accordance with one aspect of the invention.

Referring to FIG. 1, there is illustrated, in the form of a flow chart, a procedure for the purification of the chlamydial outer membrane antigen extract (MAE) Thus, purified elementary bodies (EBs) are resuspended in 10 mM phosphate buffer, pH 7.4, and made to 1 wt % Sarkosyl, 10 mm dithiothreitol (DTT). The mixture is incubated at 37° C. for from about 30 minutes to about 24 hours, with occasional 20-second pulses in a sonicating water bath. Following the incubation, soluble and insoluble fractions are separated by centrifugation at 150,000 g for 1 hour at 20° C. The insoluble fraction comprises outer membrane complexes, which are recovered as a pellet, while soluble material remains in the supernatant. The insoluble fraction is resuspended in 10 mM phosphate buffer, pH 7.4, containing 10 mM DTT, and decanoyl-N-methylglucamide (Mega 10) and/or octyl glucoside at a total combined concentration of about 1 wt %. The resuspended material is incubated at 37° C. for from about 30 minutes to about 24 hours, with occasional 20-second pulses in a sonicating water bath. Following the incubation, soluble and insoluble fractions are separated by centrifugation at 150,000 g for 1 hour at 20° C. The material remaining in the supernatant is the MAE.

Figure 2A:
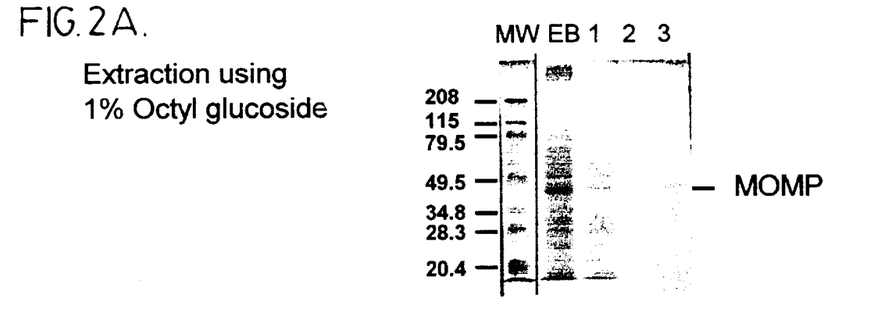
FIGS. 2A, 2B and 2C are SDS-PAGE gels showing the results of preparing the MAE using octyl glucoside (FIG. 2A), Mega 10 (FIG. 2B), or a mixture of the two (FIG. 2C) to extract the outer membrane complexes in the purification scheme of FIG. 1. MW=molecular weight markers (kDa); EB=elementary bodies; Lane 1=soluble fraction obtained after Sarkosyl extraction; Lane 2=membrane antigen extract; Lane 3=insoluble fraction containing residual membrane associated material.
Figure 2B:
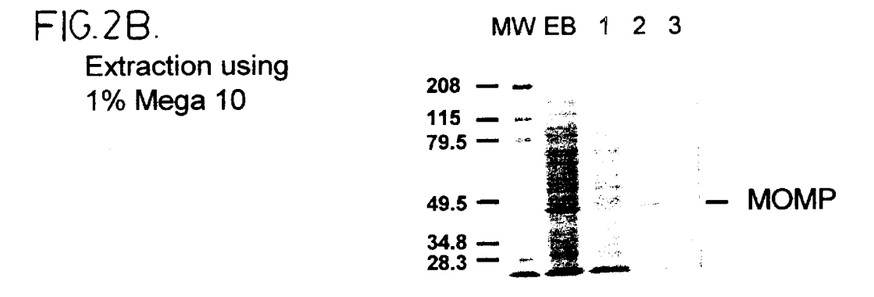
Figure 2C:
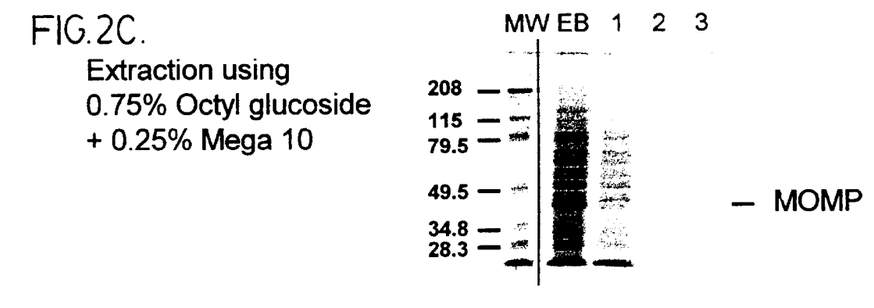

FIGS. 2A, 2B and 2C illustrates the preparation of MAE using octyl glucoside, Mega 10, or a mixture of the two detergents, to extract the membrane antigens from the Sarkosyl-insoluble pellet. When the MAE is prepared using Mega 10 alone, or a mixture of octyl glucoside and Mega 10 in, for example, the ratio 1:3, the final insoluble pellet contains less MOMP than when only octyl glucoside is used. MW=molecular weight markers; EB=elementary bodies; Lane 1=soluble fraction obtained after Sarkosyl extraction; Lane 2=membrane antigen extract; Lane 3=insoluble fraction containing residual membrane associated material.

Figure 3:
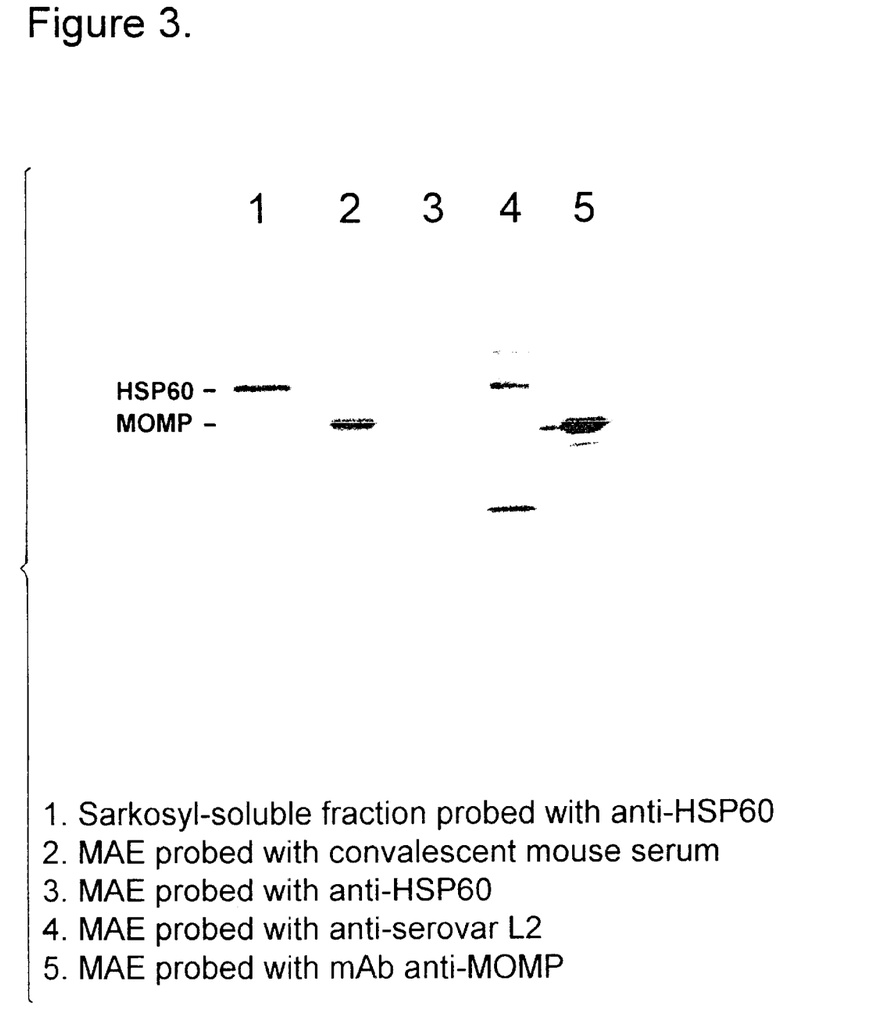

FIG. 3 illustrates the composition of the MAE as determined by immunoblotting. Using a rabbit antiserum specific for the cytoplasmic protein HSP60 shows that there is HSP60 in the Sarkosyl-soluble fraction (lane 1) but not in the MAE (lane 3). The major component of the MAE is the chlamydial major outer membrane protein (MOMP) as shown by immunoblotting with pooled strain-specific convalescent mouse antisera (lane 2) or with a MOMP-specific monoclonal antibody (lane 5). However, several other antigenic components of the MAE can be demonstrated using sera raised to the homologous strain of chlamydia (lane 2) or to a heterologous strain (lane 5).

Figure 4:
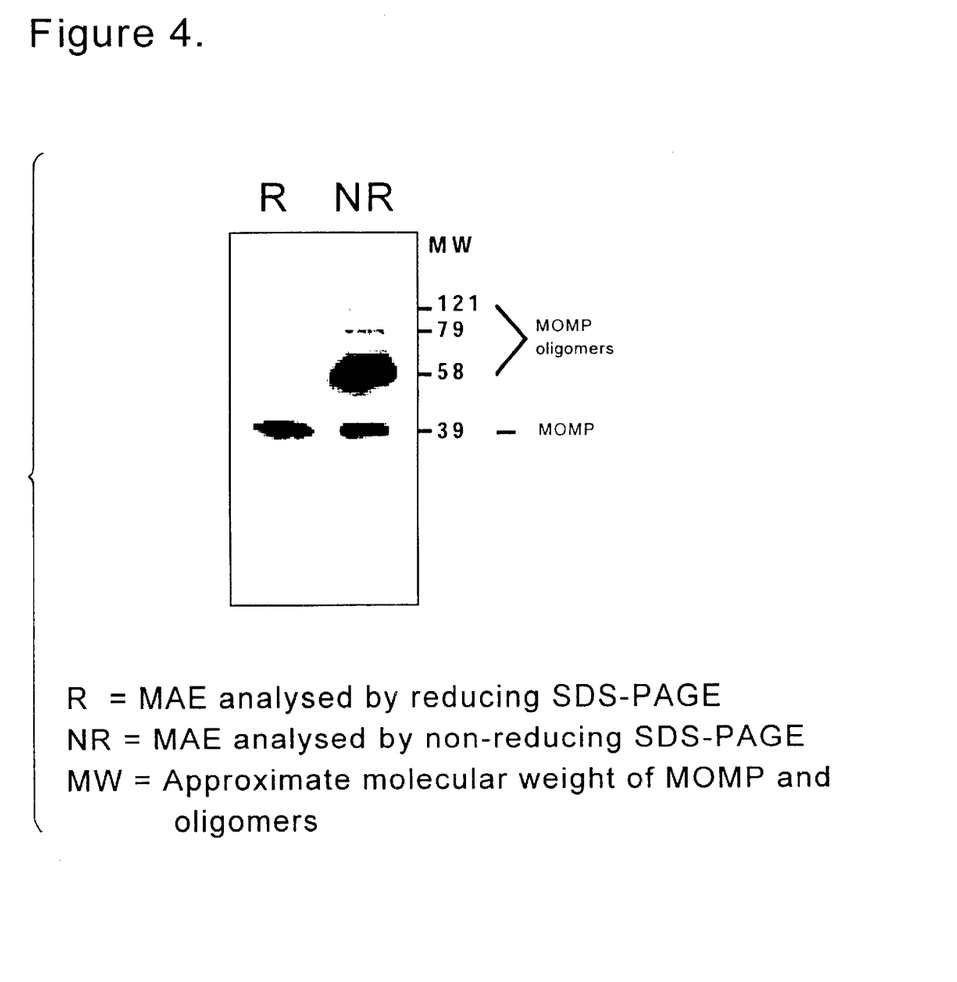
FIG. 4 shows the results of an immunoblot conducted under reducing and non-reducing conditions demonstrating that MOMP in the MAE is present as oligomers (lane NR) with a molecular weights greater than that of monomeric MOMP (lane R). The indicated molecular weights (kDa) are actual molecular weights for the materials.

FIG. 4 shows the results of an immunoblot conducted under reducing and non-reducing conditions. These results demonstrate that MOMP in the MAE is present as oligomers (lane NR) with molecular weights ranging from 45 to 125 kDa. Monomeric MOMP of molecular weight about 39,000 Da is shown in Lane R.

Figure 5A:
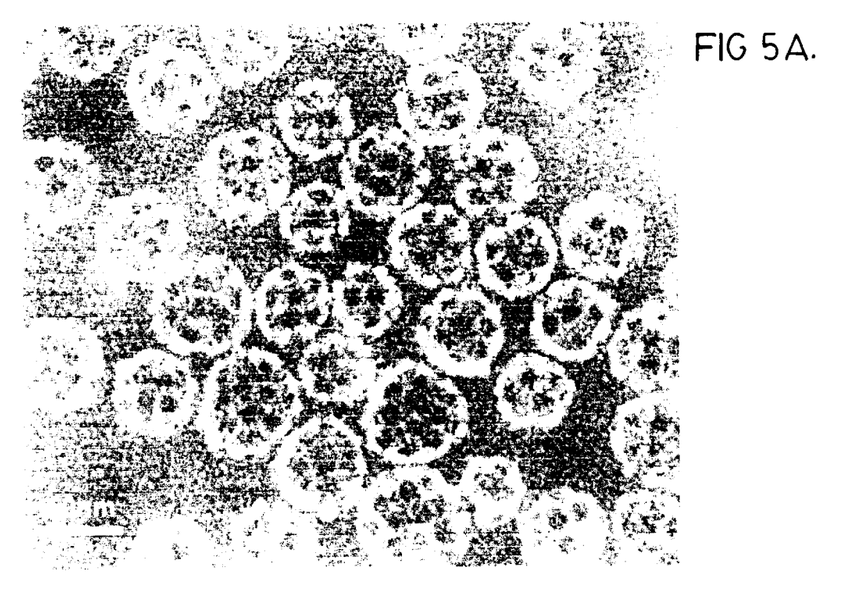
FIGS. 5A abd 5B are photomicrographs of ISCOMs prepared using the methods of Morein (ref. 36) (FIG. 5A) or of Mowat and Reid (ref. 37) (FIG. 5B), as described in the Examples below, and provided in accordance with an aspect of the present invention.
Figure 5B:
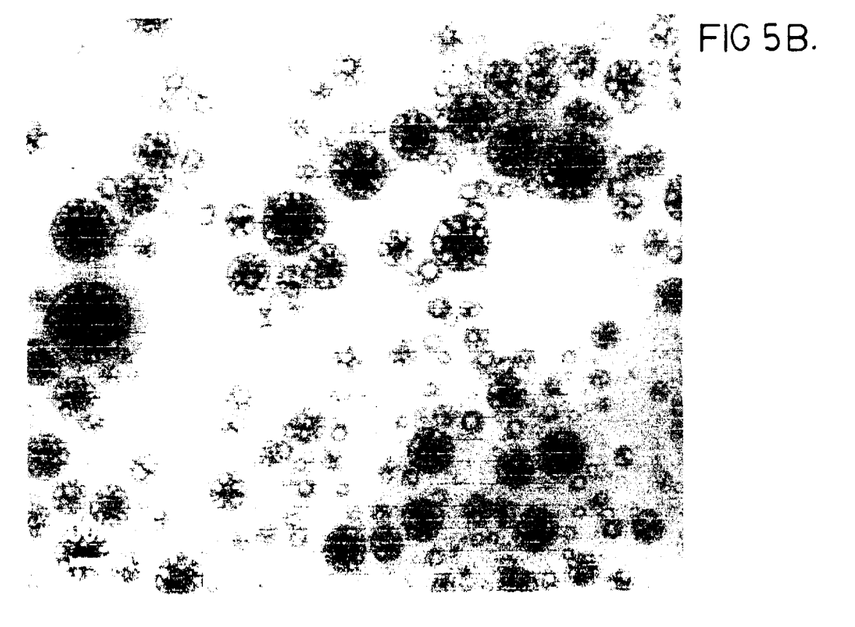
Figure 6A:
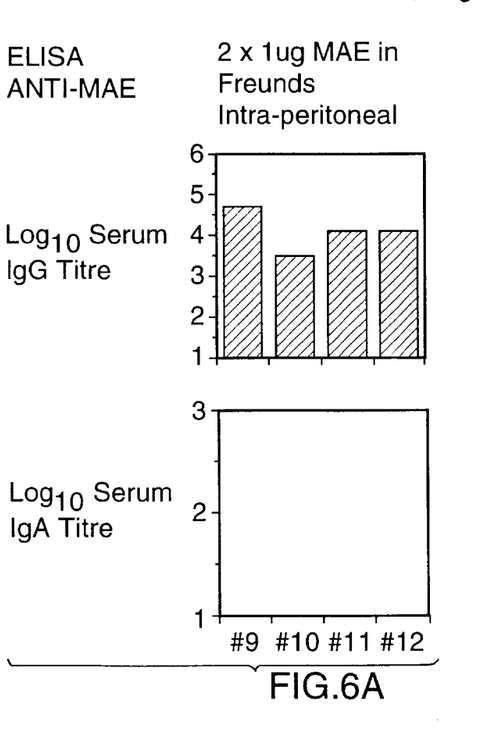
FIGS. 6A, 6B and 6C are bar graphs showing the immunogenicity of ISCOMs containing MAE administered to mice intra-nasally or intra-peritoneally, in comparison to Freund's adjuvanted MAE administered intra-peritoneally. ISCOMs administered by either route elicit both IgG and IgA in vaginal secretions.
Figure 6B:
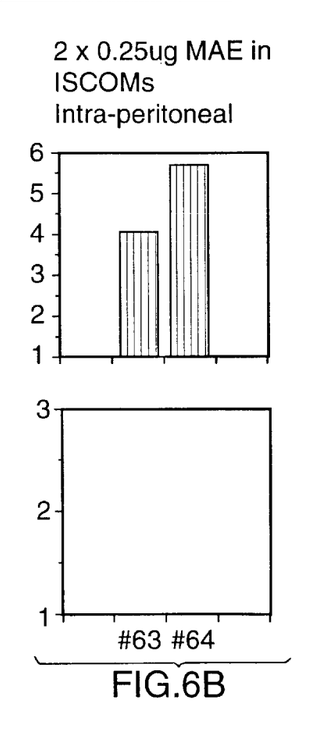
Figure 6C:
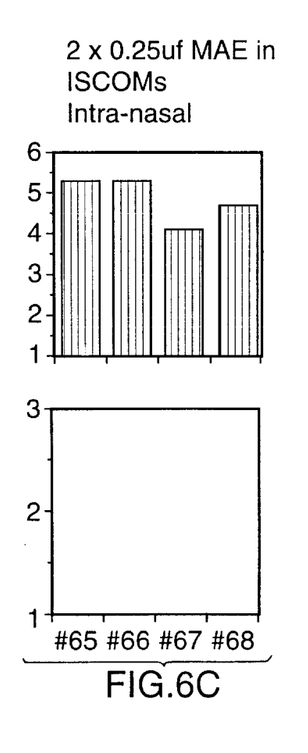
Figure 6D:
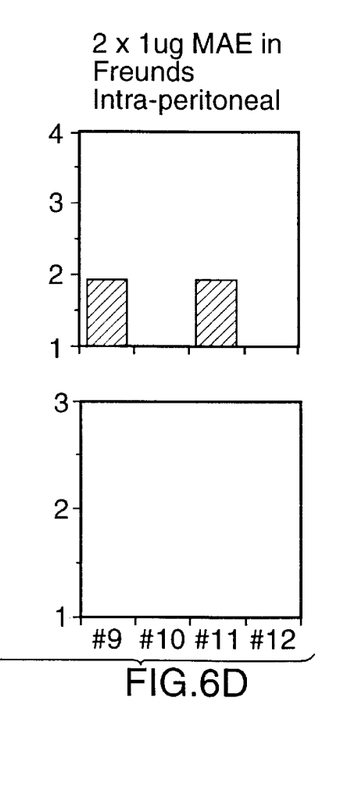
Figure 6E:
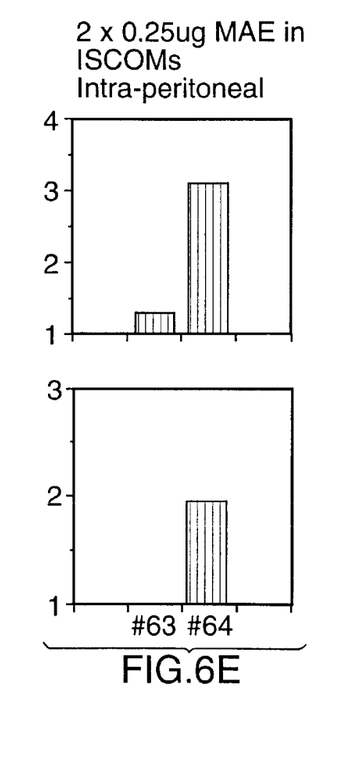
Figure 6F:
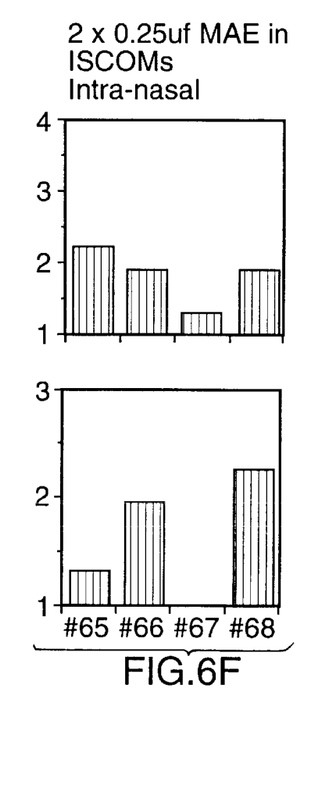

FIGS. 5A and 5B illustrates ISCOMs containing MAE prepared using the methods of More:in (ref. 36) (FIG. 5A) or of Mowat and Reid (ref. 37) (FIG. 5B). When following the method of Morein, ISCOMs are prepared by diluting the MAE to about 0.2 mg/mL with 10 mM phosphate buffer pH 6.8. phosphatidyl choline and cholesterol are dissolved at about 5 mg/mL each in approximately 20% Mega 10 then added to the diluted MAE to a final concentration of about 0.2 mg/mL each. Quil A is added to a concentration of about 1 mg/mL. Sufficient 20% Mega 10 is then added to bring the final concentration in the mixture to about 1%. The mixture is incubated with shaking at room temperature overnight then dialysed at 20° to 25° C. against three changes of 10 mM phosphate buffer, pH 6.8, for from about 2 hours to about 20 hours per change. When prepared according to this method the ISCOMs are uniform particles about 40 to 50 nm in diameter.

When following the method of Mowat and Reid, the membrane antigen extract: is adjusted to a protein concentration of about 0.5 to 1 mg/mL and to a detergent concentration of about 2%. Quil A is added to a concentration of about 1 mg/mL. phosphatidyl choline and cholesterol are dissolved at about 10 mg each per mL in approximately 2% Mega 10 or octyl glucoside, then added to the membrane antigen extract at a concentration of about 0.5 mg each per mL. The mixture is mixed, then dialysed at 20° to 25° C. against six changes of 50 mM Tris-HCl, pH 8.5 for about from about 6 hours to about 18 hours per change. When prepared according to this method the ISCOMs vary in diameter from about 30 nm to about 200 nm.

FIGS. 6A, 6B, 6C, 6D, 6E and 6F shows the immunogenicity of ISCOMs containing MAE administered to mice either intranasally or intraperitoneally. Female A/J mice were inoculated with MAE-ISCOMs containing about 0.25 µg of protein by the intraperitoneal (mice #63–64) or the intranasal (mice #65–68) routes on days 1 and 14, or with MAE containing about 1 µg of protein in complete Freund's adjuvant on day 1 and with MAE containing about 1 µg of protein in incomplete Freund's adjuvant on day 14 (mice #9–12). Sera and vaginal washes were taken on days 0 and 28, and assayed in an ELISA assay for MAE-specific serum IgG, serum IgA, vaginal IgG and vaginal IgA. The MAE-ISCOMs induce serum IgG titres comparable to those induced by the higher dose of MAE in Freund's, and consistently induce vaginal IgG and IgA, which MAE in Freund's did not.

Advantages of the MAE-ISCOMs of the present invention include the capability to induce a strong and protective anti-chlamydial immune response when administered to a mammal without exacerbating chlamydial disease, by, for example, potentiation of chlamydial disease by sensitising vaccinees to HSP60.

It is clearly apparent to one skilled in the art, that the various embodiments of the present invention have many applications in the fields of vaccination, diagnosis, treatment of Chlamydia infections and the generation of immunological reagents. A further non-limiting discussion of such uses is further presented below.

1. Vaccine preparation and Use

Immunogenic compositions, suitable to be used as vaccines, may be prepared from immunogenic outer membrane antigen extracts of Chlamydia, including the major outer membrane protein (MOMP), as disclosed herein. The immunogenic composition elicits an immune response which produces antibodies, including anti-MOMP antibodies, IgG and IgA antibodies, and antibodies that are opsonizing or bactericidal. Should the vaccinated subject be challenged by Chlamydia, the antibodies bind thereto and thereby inactivate the Chlamydia. Furthermore, opsonizing or bactericidal antibodies may also provide protection by alternative mechanisms. The immunogenic compositions also produce cell mediated immune responses including CD4+ and CD8+ T cell response including cytotoxic T cell responses specific for MOMP.

Immunogenic compositions including vaccines may be prepared as injectables, as liquid solutions or emulsions. The outer membrane antigen extracts may be mixed with pharmaceutically acceptable excipients which are compatible therewith. Such excipients may include, water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and vaccines may be administered parenterally, by injection subcutaneously or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Such suppositories may be formed from mixtures containing the active ingredient(s) in the range of about 0.5 to about 10%, preferably about 1 to 2%. Oral formulations may include normally employed incipients such as, for example, pharmaceutical grades of saccharine, cellulose and magnesium carbonate. These compositions can take the form of solutions, suspensions, tablets, pills, capsules, sustained release formulations or powders and contain about 1 to 95% of the outer membrane antigen extract, preferably about 20 to about 75%.

The immunogenic preparations and vaccines are administered in a manner compatible with the dosage formulation, and in such amount as will be therapeutically effective, protective and immunogenic. The quantity to be administered depends on the subject to be treated, including, for example, the capacity of the individual's immune system to synthesize antibodies and if needed, to produce a cell-mediated immune response. precise amounts of active ingredient required to be administered depend on the judgment of the practitioner. However, suitable dosage ranges are readily determinable by one skilled in the art and may be of the order of micrograms of the outer membrane antigen extract per vaccination. Suitable regimes for initial administration and booster doses are also variable, but may include an initial administration followed by subsequent administrations. The dosage may also depend on the route of administration and will vary according to the size of the host.

The concentration of the outer membrane antigen extracts in an immunogenic composition according to the invention is in general about 1 to 95%. A vaccine which contains antigenic material of only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

Thus, the immunogenic compositions provided herein may be formulated to comprise at least one additional immunogen, which may comprise or be derived from bacterial, viral or protozal pathogens including a paramyxovirus, polio, hepatitis B, bacterial toxoids, including diphtheria toxoid and tetanus toxoid, influenza, haemophilus, pertussis, pneumococcus, mycobacteria, hepatitis A, HIV, HSV, *Neisseria gonorrhoea, Treponema pallidum,* and organisms which result in other sexually transmitted diseases.

Immunogenicity can be significantly improved if the antigens are co-administered with adjuvants, commonly used as 0.05 to 0.1 percent solution in phosphate-buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and a HBsAg vaccine has been adjuvanted with alum. While the usefulness of alum is well established for some applications, it has limitations. For example, alum is ineffective for influenza vaccination and inconsistently elicits a cell mediated immune response. The antibodies elicited by alum-adjuvanted antigens are mainly of the IgG1 isotype in the mouse, which may not be optimal for protection by some vaccinal agents.

A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes.

2. Immunoassays

The outer membrane antigen extracts of the present invention are useful as immunogens for the generation of anti-Chlamydia antibodies and as antigens in immunoassays including enzyme-linked immunosorbent assays (ELISA), RIAs and other non-enzyme linked antibody binding assays or procedures known in the art for the detection of anti-Chlamydia antibodies. In ELISA assays, the outer membrane antigen extract is immobilized onto a selected surface, for example, a surface capable of binding proteins such as the wells of a polystyrene microtiter plate. After washing to remove incompletely adsorbed antigen, a nonspecific protein such as a solution of bovine serum albumin (BSA) that is known to be antigenically neutral with regard to the test sample may be bound to the selected surface. This allows for blocking of nonspecific adsorption sites on the immobilizing surface and thus reduces the background caused by nonspecific bindings of antisera onto the surface.

The immobilizing surface is then contacted with a sample, such as clinical or biological materials, to be tested in a manner conducive to immune complex (antigen/antibody) formation. This may include diluting the sample with diluents, such as solutions of BSA, bovine gamma globulin (BGG) and/or phosphate buffered saline (PBS)/Tween. The sample is then allowed to incubate for from 2 to 4 hours, at temperatures such as of the order of about 25° to 37° C.

Following incubation, the sample-contacted surface is washed to remove non-immunocomplexed material, The washing procedure may include washing with a solution, such as PBS/Tween or a borate buffer. Following formation of specific immunocomplexes between the test sample and the bound outer membrane antigen extract, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity such as an enzymatic activity that will generate, for example, a colour development upon incubating with an appropriate chromogenic substrate. Quantification may then be achieved by measuring the degree of colour generation using, for example, a spectrophotometer.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of protein biochemistry and immunology used but not explicitly described in this disclosure and these Examples are amply reported in the scientific literature and are well within the ability of those skilled in the art.

Example 1

This Example illustrates the preparation of the membrane antigen extract from chlamydial elementary bodies, as shown in FIG. 1.

Purified elementary bodies (EBs), prepared as described in ref. 19, were resuspended in 10 mM phosphate buffer, pH 7.4, and made to 1 wt % Sarkosyl (N-Lauylsarosine, sodium salt), 10 mM DTT. The EBs were incubated at 37° C. for about 90 minutes, with occasional 20 second pulses in a sonicating water bath. Following the incubation, soluble and insoluble fractions were separated by centrifugation at 150,000 g for 1 hour at 20° C. The insoluble fraction comprises outer membrane complexes which are recovered as a pellet, while soluble material comprising principally cytoplasmic proteins including HSP60, remains in the supernatant. The insoluble fraction was resuspended in 10 mM phosphate buffer, pH 7.4, containing 10 mM DTT, and decanoyl-N-methylglucamide (Mega 10) and/or octyl glucoside at a total combined concentration of about 1 wt %. The resuspended material was incubated at 37° C. for about 90 minutes, with occasional 20-second pulses in a sonicating water bath. Following the incubation, soluble and insoluble fractions were separated by centrifugation at 150,000 g for 1 hour at 20° C. The soluble material remaining in the supernatant was the membrane antigen extract while the insoluble fraction contained residual membrane-associated material.

Example 2

This Example illustrates the preparation of ISCOMs with the membrane antigen extract according to the methods of Morein (ref. 36) or of Mowat and Reid (ref. 37).

When following the method of Morein, ISCOMs were prepared by diluting the MAE, prepared as described in Example 1, to about 0.2 mg/ml with 10 mM phosphate buffer pH 6.8. phosphatidyl choline and cholesterol were dissolved at about 5 mg/ml each in approximately 20% Mega 10 and then added to the diluted MAE to a final concentration of 0.2 mg/ml each. Quil A (a complex but purified mixture of Quillaja saponins which are glycosides of quillaic acid and carbohydrates) was added to a concentration of about 1 mg/ml. Sufficient 20% Mega 10 was then added to bring the final concentration in the mixture to about 1 % wt. The mixture was shaken at room temperature overnight and then dialysed at 20 to 25° C. against three changes of 10 mM phosphate buffer, pH 6.8, for about 6 hours, about 16 hours and about 6 hours for the three buffer changes. When prepared according to this method, the ISCOMs were uniform particles about 40 to 50 nm in diameter.

When following the method of Mowat and Reid, the membrane antigen extract, prepared as described in Example 1, was diluted to a protein concentration of about 0.5 to 1 mg/ml and to a detergent concentration of about 2 wt %. Quil was added to a concentration of about 1 mg/ml. phosphatidyl choline and cholesterol were dissolved at about 10 mg each per ml in approximately 2% Mega 10 or octyl glucoside, then added to the membrane antigen extract at a concentration of about 0.5 mg each per ml. The mixture was mixed briefly, then dialysed at 20 to 25° C. against six changes of 50 mM Tris-HCl, pH 8.5 alternately for about 6 hours and about 18 hours per buffer change. When prepared according to this method, the ISCOMs vary in diameter from about 30 nm to about 200 nm.

Electron micrographs of ISCOMs formed by both methods are shown in FIGS. 5A and 5B. FIG. 5A shows the ISCOMs prepared according to the procedure of Morein and FIG. 5B shows the ISCOMs prepared according to the procedure of Mowat and Reid.

Example 3

This Example illustrates the immunogenicity of chlamydial membrane antigen extract (MAE) -ISCOMs in mice.

Female A/J mice were immunized with MAE-ISCOMs, prepared as described in Example 2 following the procedure of Mowat and Reid, containing about 0.25 μg of protein by the intraperitoneal (mice #63–64) or the intranasal (mice #65–68) routes on days 1 and 14, or with MAE containing about 1 μg of protein in complete Freund's adjuvant on day 1 and with MAE containing about 1 μg of protein in incomplete Freund's adjuvant on day 14 (mice #9–12). Sera and vaginal washes were taken on days 0 and 28, and assayed in an ELISA assay for MAE-specific serum IgG, serum IgA, vaginal IgG and vaginal IgA.

As may be seen from the results obtained (FIGS. 6A, 6B and 6C), the MAE-ISCOMs provided herein induced serum IgG titres comparable to those induced by the higher dose of MAE in Freund's (upper panels), and consistently induced vaginal IgG (penultimate panels). MAE in Freund's adjuvant did not induce any IgA antibodies whereas the MAE-ISCOMs produced IgA antibodies (lower panels).

Example 4

This Example illustrates the use of MAE-ISCOMs to protect mice from chlamydial infection.

A group of 120 female mice, aged 6 to 8 weeks, are divided into two groups of 60, designated infected and uninfected. On days 0 arid 7, all mice are treated with 2.5 mg progesterone administered subcutaneously. On day 7, the infected group is vaginally inoculated with 1000 $ID_{50}$ of *Chlamydia trachomatis* MoPn strain and the uninfected group is vaginally inoculated with SPG buffer. Inoculations are performed under light anaesthesia. The animals are then rested until day 91, when they are further divided into twelve groups and vaccinated as follows:

10 infected mice receive intramuscularly MAE-ISCOMs, 10 infected mice receive intranasally MAE-ISCOMs, 10 infected mice receive MAE, prepared as described in Example 1, mixed with ISCOM matrix, intramuscularly, 10 infected mice receive MAE, prepared as described in Example 1, mixed with ISCOM matrix, intranasally, 10 infected mice receive ISCOM matrix intramuscularly, 10 infected mice receive ISCOM matrix intranasally, 10 uninfected mice receive intramuscularly MAE-ISCOMs, prepared by the procedure of Morein as described in Example 2, 10 uninfected mice receive intranasally MAE-ISCOMs, prepared by the procedure of Morein as described in Example 2, 10 uninfected mice receive MAE, prepared as described in Example 1, mixed with ISCOM matrix, intramuscularly, 10 uninfected mice receive MAE, prepared as described in Example 1, mixed with ISCOM matrix, intranasally, 10 uninfected mice receive ISCOM matrix intramuscularly, 10 uninfected mice receive ISCOM matrix intranasally.

The ISCOM matrix is prepared in the same way as the MAE-ISCOMs as in Example 2 except that MAE is omitted from the reaction mixture. MAE mixed with ISCOM matrix is prepared by adding MAE to preformed ISCOM matrix. Each dose of vaccine contains about 2 µg of MAE and about 10 µg of saponin. These vaccinations are repeated on days 112 and 133. Blood and vaginal washes are taken just before each vaccination.

All mice are challenged with about 100 $ID_{50}$ of *Chlamydia trachomatis* MoPn strain, administered vaginally to anaesthetized animals on days 145, 147 and 149. On days 154 and 161 three mice from each of the 12 groups are necropsied. On day 168 all remaining mice are necropsied. At necropsy, the reproductive tract is removed and divided into parts so that symptoms due to infection can be determined by examination of histological sections and the presence of chlamydiae in the tract can be assessed immunologically and by PCR assay.

SUMMARY OF INVENTION

In summary of this disclosure, the present invention provides ISCOM, chlamydial major outer membrane protein complexes, useful in vaccines against chlamydial diseases, and in the preparation of immunological reagents. Modifications are possible within the scope of the invention.

REFERENCES

1. Grayston, J. T. and S. -P Wang. 1975. New knowledge of chlamydiae and the diseases they cause. J. Infect. Dis., 132: 87–104.
2. Grayston, J. T., S. -P Wang, L. -J. Yeh, and C. -C. Kuo. 1985. Importance of reinfection in the pathogenesis of trachoma. Rev. Infect. Dis. 7:717-
3. Taylor, H. R., S. L. Johnson, R. A. prendergast, J. Schachter, C. R. Dawson and A. M. Silverstein, 1982. An Animal Model of Trachema. II. The importance of repeated infection. Invest. Opthalmol. Visual. Sci. 23 507–515.
4. Taylor, H. R., R. A. prendergast, C. R. Dawson, J. Schachter and A. M. Silverstein, 1981. An Animal Model for Cicatrizing Trachoma. Invest. Opthalmol. Sci. 21 422–433.
5. Caldwell, H. D., S. Stewart, S. Johnson and H. Taylor. 1987. Tear and serum antibody response to *Chlamydia trachomatis* antigens during acute chlamydial conjunctivitis in monkeys as determined by immunoblotting. Infect. Immun. 55: 93–98.
6. Wang, S. -P., C. -C. Kuo, R. C. Barnes, R. S. Stephens and J. T. Grayston. 1985. Immunotyping of *Chlamydia trachomatis* with monoclonal antibodies. J. Infect. Dis 152:791–800.
7. Nichols, R. L., R. E. Oertley, C. E. O. Fraser, A. B. MacDonald, and D. E. McComb. 1973. Immunity to chlamydial infections of the eye. VI. Homologous neutralization of trachoma infectivity for the owl monkey conjunctivae by eye secretions from humans with trachoma. J. Infect. Dis. 127: 429–432.
8. Orenstein, N. S., J. D. Mull and S. E. Thompson III. 1973. Immunity to chlamydial infections of the eye. V. passive transfer of antitrachoma antibodies to owl monkeys. Infect. Immun. 7:600–603.
9. Ramsey, K H, Rank, R. G., (March 1991). Resolution of Chlamydia Genital Infection with Antigen-Specific T-Lymphocyte Lines. Infect. and Immun. 59:925–931
10. Magee, D M, William, D M, Smith, J G, Bleicker, C A, Grubbs, B G, Schachter, J. and Rank, R G., (1995). Role of CD8 T Cells in primary Chlamydia Infection. Infect. Immun. February 1995. 63: 516–521
11. Su, H. and Caldwell, H D., (1995) CD4+T Cells play a Significant Role in Adoptive Immunity to *Chlamydia trachomatis* Infection of the Mouse Genital Tract. Infect. Immun. September 1995, 63: 3302–3308
12. Magee, D M, Williams, D M., Smith J G., Bleicker, C A., Grubbs, B G, Schachter, J. and Rank, R G., (1995) Role of CD8 T Cells in primary Chlamydia Infection., Infect. Immun. February 1995. 63: 516–521
13. Beatty, P R., and Stephens R S., 1994, CD8+ T Lymphocyte-Mediated Lysis of Chlamydia-Infected L Cells Using an Endogenous Antigen pathway., Journal of Immun. 1994, 153:4588.
14. Starnbach, M N. Bevan, M J. and Lampe, M F. (1994), protective Cytotoxic T. Lymphocytes are Induced During Murine Infection with *Chlamydia trachomatis*, Journal of Immun. 1994, 153:5183.
15. Starnbach, M N. Bevan, M J. and Lampe, M F., (1995), Murine Cytotoxic T. Lymphocytes Induced Following *Chlamydia trachomatis* Intraperitonal or Genital Tract Infection Respond to Cells Infected with Multiple Serovars., Infect. & Immun. September 1995, 63: 3527–3530.
16. Igietseme, J U, (1996), Molecular mechanism of T-cell control of Chlamydia in mice: role of nitric oxide in vivo. Immunology 1996, 88:1–5
17. Igietseme, J U, (1996), The Molecular mechanism of T-cell control of Chlamydia in mice: role of nitric oxide. Immunology 1996, 87:1–8.
18. Ward, M. E. 1992. Chlamydial vaccines—future trends. J. Infection 25, Supp. 1:11–26.
19. Caldwell, H. D., J. Kromhout and J. Schachter. 1981. Purification and partial characterization of the major outer membrane protein of *Chlamydia trachomatis*. Infect. Immun. 31:1161–1176.
20. Bavoil, p., Ohlin, A. and Schachter, J., 1984. Role of Disulfide Bonding in Outer Membrane Structure and permeability in *Chlamydia trachomatis*. Infect. Immun., 44: 479–485
21. Campos, M., Pal, Sukumar, O'Brian, T. P., Taylor, H. R., Prendergast, R. A., and Whittum-Hudson, J. A., 1995., A Chlamydia Major Outer Membrane protein Extract as a Trachoma Vaccine Candidate., Invest. Opthalmol. Vis. Sci. 36: 1477–1491.
22. Zhang Y. -X., S. J. Stewart, and H. D. Caldwell. 1989. Protective monoclonal antibodies to *Chlamydia trachomatis* serovar- and serogroup-specific major outer membrane protein determinants. Infect. Immun. 57:636–638.
23. Zhang, Y. -X., S. Stewart, T. Joseph, H. R. Taylor and H. D. Caldwell. 1987. Protective monoclonal antibodies recognise epitopes located on the major outer membrane protein of *Chlamydia trachomatis*. J.Immunol. 138:575–581.
24. Department of Health and Human Services. 1989. Nucleotide and amino acid sequences of the four variable domains of the major outer membrane proteins of *Chlamydia trachomatis*. Report Nos: PAT-APPL-7-324 664. National Technical Information Services, Springfield, Va.
25. Yuan, Y., Y. -X. Zhang, N. G. Watkins, and H. D. Caldwell. 1989. Nucleotide and deduced amino acid sequences for the four variable domains of the major outer membrane proteins of the 15 *Chlamydia trachomatis* serovars. Infect. Immun. 57:104–1049.
26. Su, H. and H. D. Caldwell, H. D. 1992. Immunogenicity of a chimeric peptide corresponding to T-helper and B-cell epitopes of the *Chlamydia trachomatis* major outer membrane protein. J. Exp. Med. 175:227–235.
27. Su, H., N. G. Watkins, Y. -X. Zhang and H. D. Caldwell. 1990. *Chlamydia trachomatis*-host cell interactions: role of the chlamydial major outer membrane protein as an adhesin. Infect.Immun. 58:1017–1025.
28. Peeling, R., I. W. McClean and R. C. Brunham. 1984. In vitro neutralization of *Chlamydia trachomatis* with monoclonal antibody to an epitope on the major outer membrane protein. Infect.Immun. 46:484–488.
29. Lucero, M. E. and C. -C. Kuo. 1985. Neutralization of *Chlamydia trachomatis* cell culture infection by serovar specific monoclonal antibodies. Infect. Immun. 50: 595–597.
30. Baehr, W., Y. -X. Zhang, T. Joseph, H. Su, F. E. Nano, K. D. E. Everett and H. D. Caldwell. 1988. Mapping antigenic domains expressed by *Chlamydia trachomatis* major outer membrane protein genes. proc. Natl. Acad. Sci. USA, 85:4000–4004.
31. Stephens., R. S., E. A. Wagar and G. K. Schoolnik. 1988. High-resolution mapping of serovar-specific and common antigenic determinants of the major outer membrane protein of *Chlamydia trachomatis*. J. Exp. Med. 167:817–831.
32. Conlan, J. W., I. N. Clarke and M. E. Ward. 1988. Epitope mapping with solid-phase peptides:
identification of type-, subspecies-, species-, and genus-reactive antibody binding domains on the major outer membrane protein of *Chlamydia trachomatis*. Mol. Microbiol. 2: 673–679.
33. Conlan, J. W., S. Ferris, I. N. Clarke, and M. E. Ward. 1990. Isolation of recombinant fragments of the major outer membrane protein of *Chlamydia trachomatis:* their potential as subunit vaccines. J. Gen. Microbial. 136: 2013–2020.
34. Morrison, R. P., D. S. Manning, and H. D. Caldwell. 1992. Immunology of *Chlamydia trachomatis* infections. p. 57–84 In T. C. Quinn (ed) Sexually transmitted diseases. Raven press Ltd., N.Y.
35. Kersten, G. F. A. and Crommelin, D. J. A. 1995. Liposomes and ISCOMs as vaccine formulations. Biochimica et Biophysica Acta 1241 (1995) 117–138.
36. Morein, B., Fossum, C., Lovgren, K. and Hoglund, S., 1990. The iscom—a modern approach to vaccines. seminars in Virology, Vol. 1, 1990: pp 49–55.
37. Mowat & Reid, 1992. Preparation of Immune Stimulating Complexes (ISCOMs) as Adjuvants. Current protocols in Immunology 1992, Supplement 4: 2.11.1 to 2.11.12.

What we claim is:

1. An immunogenic composition, comprising an outer membrane antigen extract (MAE) of a strain of Chlamydia and an immunostimulating complex (ISCOM), said MAE comprising a major outer membrane protein (MOMP) of the strain of Chlamydia free from the heat shock protein HSP60 of the strain of Chlamydia.

2. The composition of claim 1 wherein said MOMP is in an oligomeric form.

3. The immunogenic composition of claim 2 wherein said oligomeric form of MOMP has a molecular weight of from about 45 to about 125 kDa.

4. The immunogenic composition of claim 1, wherein the outer membrane antigen extract is incorporated into immunostimulatory complexes (ISCOMs).

5. A method of protecting a host against disease caused by a strain of Chlamydia, comprising administering to said host an effective amount of the immunogenic composition of claim 1.

6. The method of claim 5 wherein said administration is to a mucosal surface of said host to produce a mucosal immune response.

7. The method of claim 6 wherein said administration to said mucosal surface is by intranasal administration to produce a vaginal tract immune response.

8. The immunogenic composition of claim 2 wherein said MOMP is complexed with at least one antigen of the strain of Chlamydia.

9. The immunogenic composition of claim 8 wherein said complex has a molecular weight of about 45 to about 125 kDa.

* * * * *